(12) United States Patent  
Kisseberth

(10) Patent No.: US 7,897,150 B1  
(45) Date of Patent: Mar. 1, 2011

(54) CANINE LYMPHOMA CELL LINE AND USES THEREOF

(75) Inventor: William C. Kisseberth, Hilliard, OH (US)

(73) Assignee: The Ohio State University, Columbus, OH (US)

( * ) Notice: Subject to any disclaimer, the term of this patent is extended or adjusted under 35 U.S.C. 154(b) by 206 days.

(21) Appl. No.: 12/082,141

(22) Filed: Apr. 9, 2008

Related U.S. Application Data

(60) Provisional application No. 60/922,497, filed on Apr. 9, 2007.

(51) Int. Cl.  
*A61K 39/395* (2006.01)  
*C12N 5/00* (2006.01)

(52) U.S. Cl. ..................... 424/172.1; 435/325

(58) Field of Classification Search ............... 424/172.1; 435/325  
See application file for complete search history.

(56) References Cited

U.S. PATENT DOCUMENTS

| | | | |
|---|---|---|---|
| 5,674,484 A * | 10/1997 | Miller et al. | ................. 424/93.1 |
| 7,220,891 B2 | 5/2007 | Barsky et al. | |
| 7,223,596 B2 | 5/2007 | Helfand et al. | |

OTHER PUBLICATIONS

Definitions document. Bioassay from http://dictionary.com.reference.com/browse/bioassay and diagnostic from http://dictionary.com.reference.com/browse/diagnostic. Online printout dated Jul. 1, 2010, pp. 1-2.*

Nakaichi M. et al., Establishment and characterization of a new canine B-cell leukemia cell line, J Vet Med Sci. 58 (5), 1996, pp. 469-471.

Momoi Y. et al., Establishment and characterization of a canine T-lymphoblastoid cell line derived from malignant lymphoma, Vet Immunology and Immunopathology, 59 (1997), pp. 11-20.

Ghernati I. et al., Characterization of a canine long-term T cell line (DLC 01) established from a dog with Sézary syndrome and producing retroviral particles, Leukemia (1999) 13, pp. 1281-1290.

Burnett R. et al., Diagnosis of Canine Lymphoid Neoplasia Using Clonal Rearrangements of Antigen Receptor Genes, Vet Pathol 40, pp. 32-41 (2003).

* cited by examiner

*Primary Examiner* — Thaian N Ton  
*Assistant Examiner* — Marcia S Noble  
(74) *Attorney, Agent, or Firm* — MacMillan, Sobanski & Todd, LLC

(57) ABSTRACT

An isolated canine peripheral T-cell lymphoma cell line, where the cell line is a canine-lymphoma cell line and uses thereof are disclosed. An isolated canine peripheral T-cell lymphoma cell line where the cell line is the canine-lymphoma cell line designated OSW (ATCC No. PTA-9116) is also disclosed.

5 Claims, 6 Drawing Sheets  
(5 of 6 Drawing Sheet(s) Filed in Color)

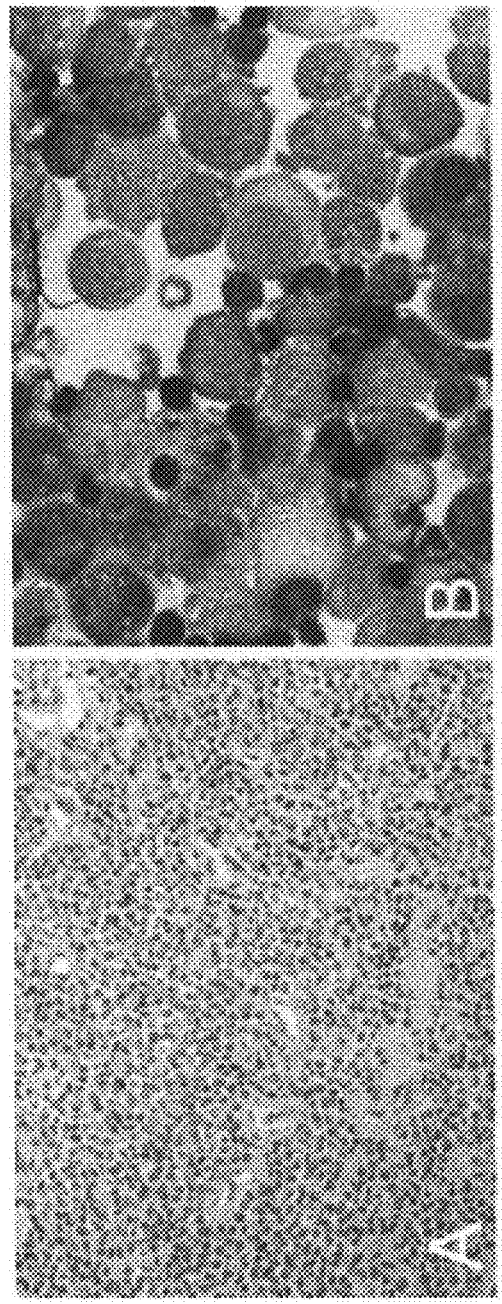
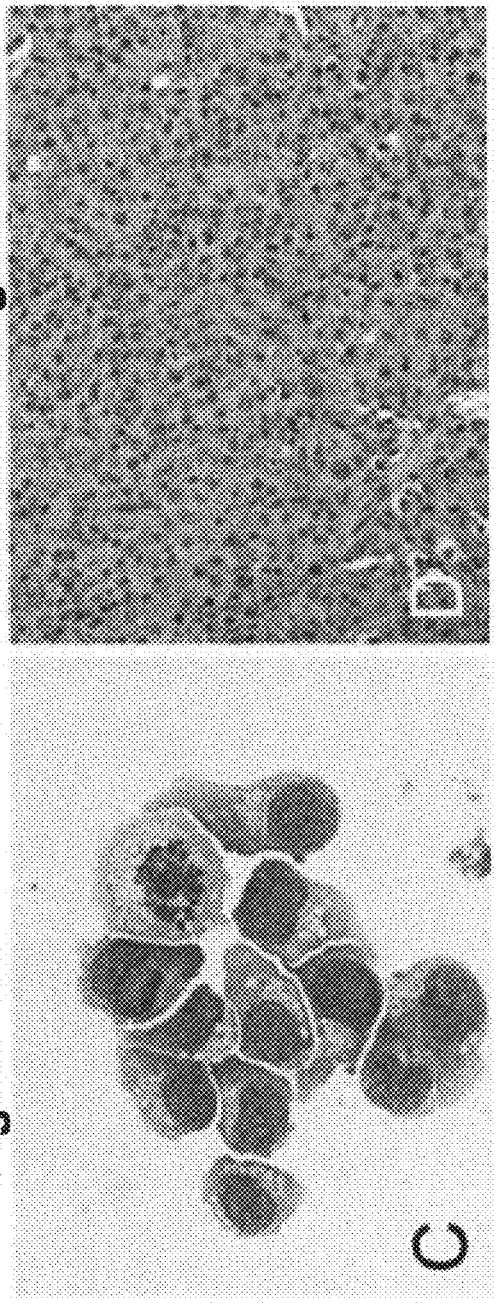
Figure 1A
Figure 1B
Figure 1C
Figure 1D

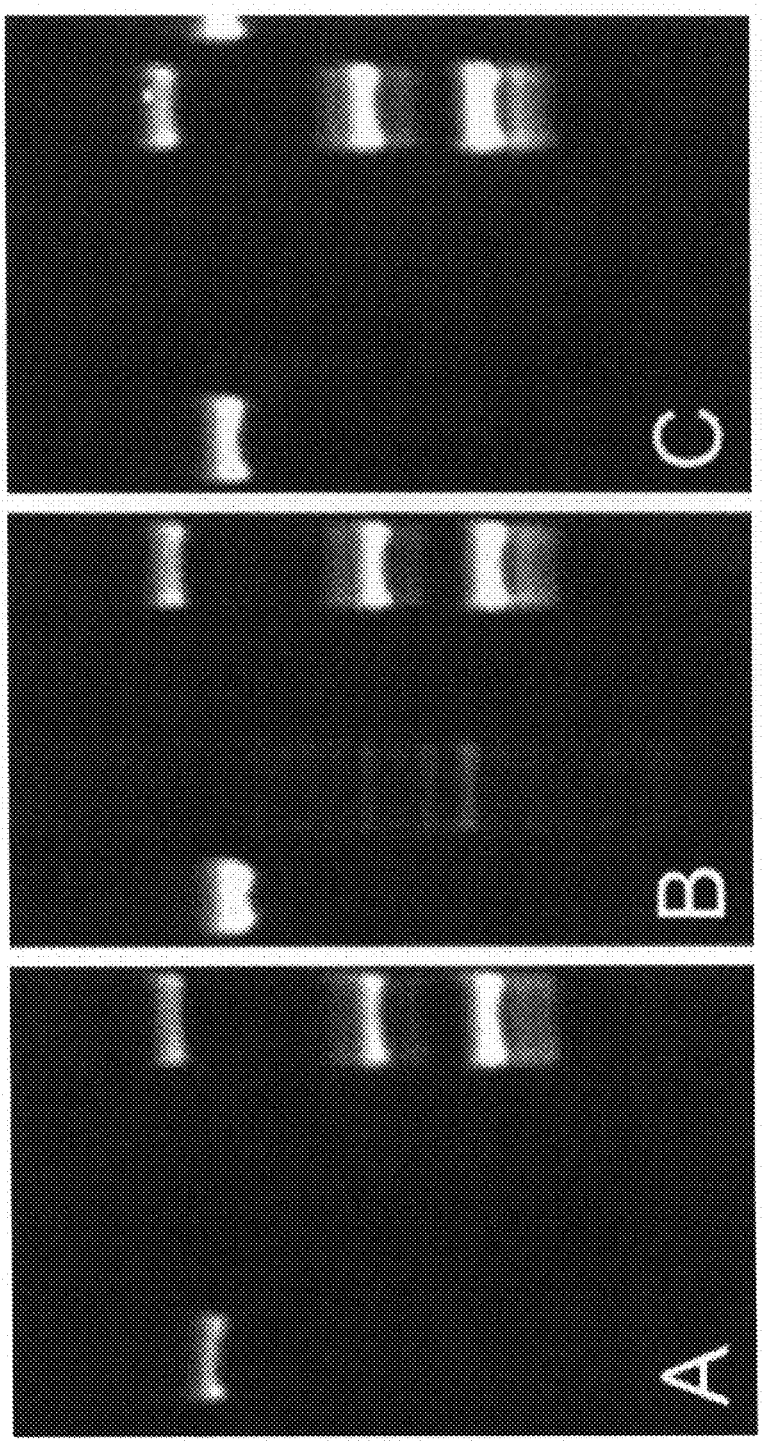

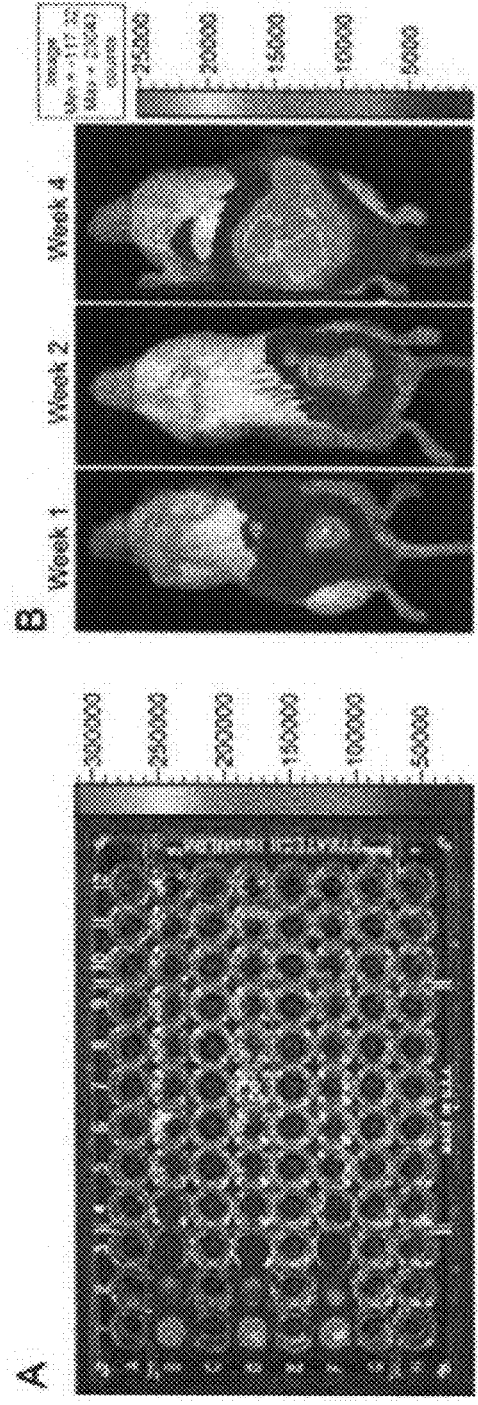
Figure 5A
Figure 5B
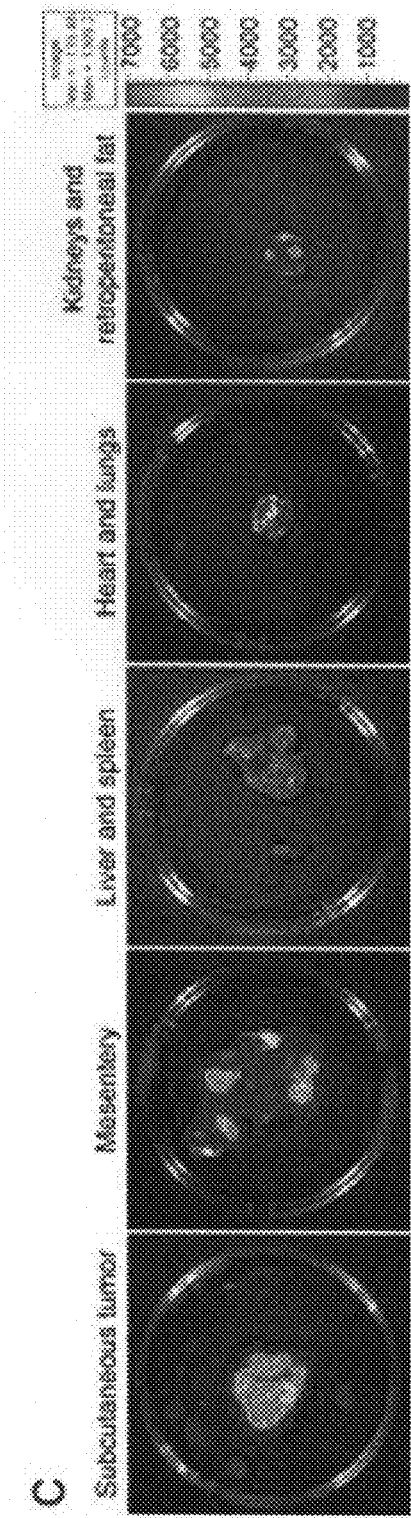
Figure 5C

CANINE LYMPHOMA CELL LINE AND USES THEREOF

CROSS-REFERENCE TO RELATED APPLICATIONS AND STATEMENT REGARDING FEDERALLY SPONSORED RESEARCH

This application claims the benefit of U.S. Provisional Application No. 60/922,497 filed Apr. 9, 2007, the disclosure of which is expressly incorporated herein by reference. This invention was made with no Government support and the Government has no rights in this invention.

TECHNICAL FIELD AND INDUSTRIAL APPLICABILITY OF THE INVENTION

This invention is directed to certain novel cell lines, methods for producing them and methods for treating or ameliorating a lymphoma and other related disorders.

BACKGROUND OF THE INVENTION

Spontaneously occurring lymphoma in the dog has many of the same histopathological, molecular, and clinical features as non-Hodgkin's lymphoma (NHL) in people [1-3]. Most of the lymphoma subtypes recognized in humans have histopathologically identical counterparts in the dog [4] and recent investigations show similar molecular characteristics in the two species [1,5]. Likewise, spontaneous lymphoma in the dog has a similar clinical presentation, response to chemotherapy, and clinical progression compared to NHL in people [1-3]. Given these similarities and the advantage of larger subject size and presence of spontaneous disease (in contrast to small subject size and experimentally induced disease in rodents), spontaneously occurring lymphoma in the dog represents an excellent large animal model for the study of lymphoma in people, including investigation of new therapeutic agents [1-3].

Laboratory study of spontaneous canine lymphoma has been severely limited by the lack of validated, well characterized, and widely disseminated cell lines. Those previously reported were either only partially characterized, were not widely distributed, or were established from leukemias, rather than lymphomas [6-9]. As in humans, establishment of new lymphoma cell lines is difficult.

In addition, despite the high incidence of lymphoma in the dog, there are relatively few reports documenting the successful establishment of cell lines from spontaneously occurring lymphoma in the dog. Those reported were either only partially characterized, not widely distributed, or established from leukemias, rather than lymphomas [6-9]. Establishment of cell lines from human leukemia/lymphomas not associated with viral etiologies (e.g., EBV, HTLV-1) is difficult (no transforming lymphotropic viruses such as EBV or HTLV-I have been conclusively identified in dogs), and most attempts fail [48]. Furthermore, many more leukemia cell lines than lymphoma cell lines have been established [48, 49]. Factors that have been proposed to enhance success in establishing leukemia/lymphoma cell lines include primary tumor cell source ("liquid" tumors and effusions being more successful), subject remission status (previous chemotherapy, relapsed tumors being more successful), and culture conditions (high $CO_2$, high serum concentrations, addition of growth factors, e.g. IL-2, IL-3, IL-6, GCSF, GM-CSF, SCF, or conditioned medium) improving success [49].

Lymphoma is the most common life-threatening cancer of dogs, accounting for up to 24% of all malignancies and over 80% of all hematopoietic cancers [50, 51]. Dogs develop virtually all subtypes of sporadic NHL seen in humans and are at greater relative risk. Furthermore, the relative risk for this disease in some breeds is up to four times higher than the average for all dogs [11, 52], suggesting that heritable risk factors for the disease have been firmly established in the derivation of specific breeds. Untreated cases, especially those of high-grade type, rarely survive beyond three months after diagnosis, but the disease is generally responsive to standard of care using CHOP-based chemotherapy protocols, increasing both the length and quality of affected dogs' lives [3].

With standard of care, remission can be achieved in >85% of canine NHL cases, and median survival ranges between 9 and 12 months [53]. This represents approximately 10% of an average canine lifetime, thus providing a tremendous opportunity to investigate new treatments in a biologically relevant large animal model. Importantly, the completion of a high (7.5×) coverage canine genome [54] has paved the way for the development of critical resources that will allow the integration of naturally occurring canine lymphoma and other cancers within the mainstream of cancer research.

By combining advances in canine genomics, establishment of canine cancer cell lines and xenograft mouse models, and initiation of clinical trials of new anticancer treatments in dogs with cancer, the study of spontaneously occurring lymphoma and other cancers in the dog will assist the development of new anticancer agents and help guide early human trials.

Therefore, there is a need to develop cell lines that can be used to study lymphoma and for developing treatments of lymphomas.

Considering the above-mentioned, there is a need for therapeutic strategies to treat lymphomas in mammals, and in particular, in canine and in humans.

Until the present invention, there have been no reports for the establishment of canine lymphoma cells or cell lines.

SUMMARY OF THE INVENTION

In various aspect, there are provided herein at least one or more of the following: an in vitro model for comparative and translational lymphoma research, a cell line for study of canine spontaneous lymphoma; a preclinical model for the development of canine therapies; a method for developing particular animal models of disease; a method for isolating lymphoma cells from canines and for establishing canine lymphoma cell lines comprising at least using an appropriate culture conditions and determining developmental stages that enable maintenance and expansion of canine lymphoma cells.

In another aspect, there is provided herein at least one or more of the following: a purified preparation comprising, or enriched for canine lymphomic cells that are capable of indefinite proliferation in vitro; a preparation of canine lymphomic cells characterized at least by being immunoreactive with markers for lymphomic cells; and, canine lymphomic cells induced to differentiate into cells of a variety of lineages in vitro or in vivo.

In yet another aspect, there is provided herein a pharmaceutical composition comprising preparations derived from the cells and cell line as described herein, and a pharmaceutically acceptable carrier, excipient, or diluent.

The cells, cell lines, and cell preparations are useful to screen for potential therapeutics that modulate development or activity of such cells or cells differentiated therefrom.

In still another aspect, there is provided herein a method for screening compounds including small molecules that affect the function of the cells described herein.

The method can include including incubating components comprising a test compound and at least one cell under conditions sufficient to allow the components to interact; and determining the effect of the compound on a function of a cell before and after incubating with the test compound.

Other aspect include a method for conducting a regenerative medicine business by identifying agents that affect the proliferation, differentiation, function, or survival of canine lymphomic cells.

Also provided herein is a method of treating a subject that includes administering an effective amount of an agent identified in accordance with a method of the invention to a subject with a disorder affecting or involving the proliferation, differentiation, function, or survival of cells of the invention.

Various objects and advantages of this invention will become apparent to those skilled in the art from the following detailed description of the preferred embodiment, when read in light of the accompanying drawings.

BRIEF DESCRIPTION OF THE DRAWINGS

The patent or application file contains at least one drawing executed in color. Copies of this patent or patent application publication with color drawing(s) will be provided by the Office upon request and payment of the necessary fee.

FIG. 1 shows the morphologic and immunophenotypic characteristics of the primary tumor and the OSW cell line in vitro and as a xenograft tumor:

FIG. 1A shows the neoplastic cells in the mediastinal tumor (A) (H&E, original magnification ×200).

FIG. 1B shows the neoplastic cells in the pleural effusion from which the OSW cell line was established (B) (Wright's-Giemsa stain, original magnification ×1000).

FIG. 1C shows the morphology of the OSW cell line (C) (Wright's-Giemsa stain, original magnification, ×1000).

FIG. 1D shows the malignant cells in the SCID-NOD xenograft tumor (D) (H&E, original magnification ×200).

FIG. 2 shows the polymerase chain reaction for antigen receptor rearrangement (PARR)— the PCR performed on genomic DNA. For each sample, lane 1—positive control for DNA, lanes 2/3—IgH gene primers, lane 4—TCRγ gene primers. An identical oligoclonal TCRγ gene rearrangement was present in all three samples:

FIG. 2A—early passage OSW cells,

FIG. 2B—lymph node biopsy,

FIG. 2C—late passage OSW cells.

FIG. 4 shows the typical SLP data demonstrating copy number and conformational status of 10 clones selected from the BAC array:

FIG. 5 shows the in vitro, in vivo, and ex vivo bioluminescent imaging of the OSW cell line:

FIG. 5A—Serial dilution of OSW cells transduced with a YFPLuc lentiviral vector. Two-fold serial dilutions of OSW cells ranging from 10,000 cells/well on the left to 5 cells/well on the right. The lowest number of cells visualized by bioluminescent imaging was between 312 and 625 cells/well (fifth and sixth wells from the left).

FIG. 5B—Serial noninvasive in vivo bioluminescent imaging of OSW cell growth following intraperitoneal injection of $5 \times 10^6$ YFP/Luc transduced OSW cells in a SCID-NOD mouse. Note that photon intensity increased over time, reflecting in vivo OSW cell growth and progression.

FIG. 5C—Ex vivo bioluminescent imaging of selected tissues after 4 weeks of YFPLuc transduced OSW cell growth in a SCID-NOD mouse. The scale to the right of each image indicates photons $s^{-1} cm^{-2}$ emission with blue corresponding to the lower level of emission and red to the highest.

DETAILED DESCRIPTION OF THE PREFERRED EMBODIMENT

Figure 3:
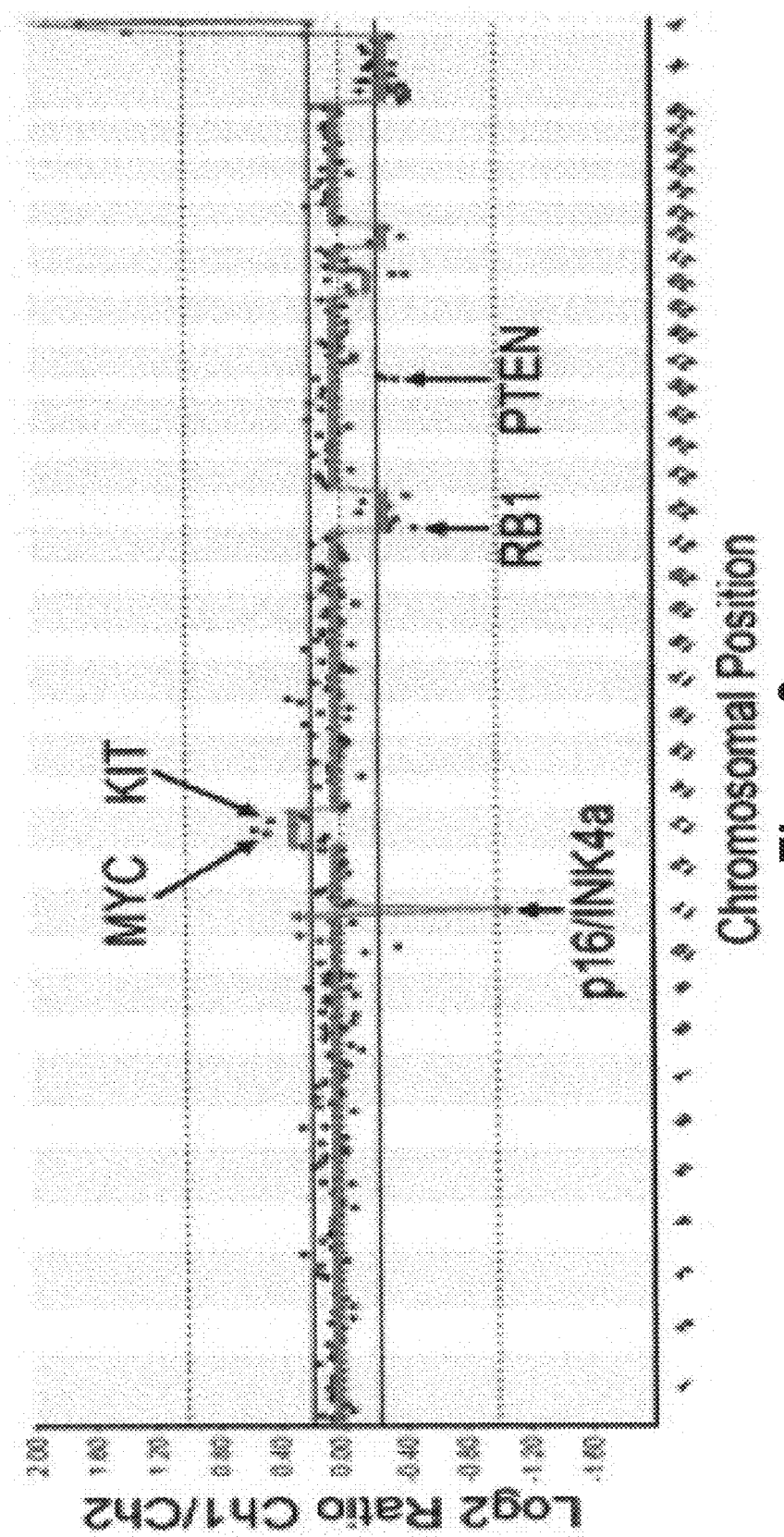
FIG. 3 shows the composite dye-swap sex mismatched aCGH profile of DNA isolated from the OSW cell line, demonstrating autosomal copy number gains on CFA 13, and copy number decreases of regions of CFA 11, 22, 26, 30 and 32. Copy number ratios for the sex chromosomes reflect the nature of the sex-mismatched hybridization. BAC clones representing p16/INK4a (CFA 11), MYC and KIT (CFA 13), RB1 (CFA 22) and PTEN (CFA 26) are indicated.

In one aspect, there is provided herein cells exhibiting a canine lymphomic cell phenotype, and cell lines comprising cells exhibiting a canine lymphomic cell phenotype. The novel canine lymphoma cell line, OSW, was established from the malignant pleural effusion of a dog with peripheral T-cell lymphoma.

The OSW canine lymphoma cell line was established from the thoracic effusion of a dog with relapsed peripheral T-cell lymphoma. Thus, the cells used to establish this cell line had several of the features associated with enhanced success for establishing human leukemia/lymphoma cell lines.

Thus, in a particular aspect, there is provided an isolated canine peripheral T-cell lymphoma cell line, wherein the cell line is the canine-lymphoma cell line designated OSW. (deposited with the ATCC under Accession No. PTA-9116 on Mar. 20, 2008). The ATCC deposit was made pursuant to the terms of the Budapest Treaty on the international recognition of the deposit of microorganism for the purposes of patent procedure. The ATCC is located at 10801 University Boulevard, Manassas Va., 20110-2209, USA. All restrictions upon public access to this cell line will be irrevocably removed upon granting of this patent application.

The OSW cell line grows rapidly in vitro and is tumorigenic as a xenograft in SCID/NOD mice. The OSW cell line provides a significant in vitro model for comparative and translational lymphoma research.

In a particular aspect, cell line is useful for the production of canine lymphoma cells that permits easier study of canine spontaneous lymphoma. Also, the OSW cell line provides a preclinical model for the development of canine therapies. In addition, the use of the OSW canine cell line enables the development of particular animal models of disease.

Also described herein are conditions for isolation of lymphoma cells from canines and for establishing canine lymphoma cell lines. More particularly, described herein are appropriate culture conditions and developmental stages that enable maintenance and expansion of canine lymphoma cells.

In another aspect, the invention further relates to a purified preparation comprised or enriched for canine lymphomic cells that are capable of indefinite proliferation in vitro. In one embodiment, a preparation of canine lymphomic cells may also be characterized by being immunoreactive with markers for lymphomic cells.

The canine lymphomic cells may be induced to differentiate into cells of a variety of lineages in vitro or in vivo. In one embodiment, the purified canine lymphomic cell are induced to differentiate into cells of various lineages where a differentiated cell preparation can be characterized by expression of genetic markers of various cell lineages In addition, lymphomic cells or cells differentiated or derived therefrom can be cultured either transiently or maintained as a cell line. Thus, the present invention also relates to cells differentiated or derived from the OSW cell line. In addition, further cells, cell lines, and cell preparations of the invention may be derived from or comprised of cells that have been genetically modified either in nature or by genetic engineering techniques in vivo or in vitro.

In an aspect, there is provided herein a method for producing canine lymphomic cell lines that exhibit a canine lymphomic cell phenotype. In certain embodiments, the method can include culturing cells from a canine lymphomic cell under conditions to promote proliferation of such cells. The method may additionally comprise inducing differentiation of the cells.

Cells exhibiting a canine lymphomic cell phenotype may be isolated by (a) obtaining a canine lymphomic cell; (b) culturing the cells under conditions, which promote proliferation of such cells; and (c) recovering the cells. In certain embodiments, the cell preparations or lines derived at all stages of development under the same culture conditions can be prepared. In addition, cells may be passaged for several months in culture.

It is also within the contemplated scope of the disclosure herein that canine transgenic cells, cell lines, or tissues can be produced using the canine lymphomic cells disclosed herein.

In addition, the cells may be used in genetic transformation techniques and may be used in the creation of canine lymphoma cell lines and to produce a genetically transformed animal as a model for human disease. Thus, it is also within the contemplated scope of the disclosure herein that an embryo (preferably an early stage embryo or expanded blastocyst) to which has been introduced one or more canine lymphomic cells of the invention; an lymphomic cell to which has been introduced by nuclear transfer a nucleus of a lymphomic cell; and a chimeric animal which is the progeny of such a blastocyst or lymphomic cell, can be provided.

The invention also provides pharmaceutical products produced by the cells, cell lines, or cell preparations of the present invention, or mitotic or differentiated cells that are progeny of the cells.

Cells, cell lines, and cell preparations may be used in both cell therapies and gene therapies aimed at alleviating disorders and diseases. As such, also disclosed herein is a method of treating a subject with a condition comprising transferring to a subject an effective amount of cells of the invention.

Also, the cells, cell lines, and cell preparations may be used as immunogens that are administered to a heterologous recipient. The cells, cell lines, and cell preparations may be used to prepare model systems of disease, in particular canine and human diseases. The cells, cell lines, and cell preparations can also be used to produce growth factors, hormones, etc.

In another aspect, there is provided herein pharmaceutical compositions comprising cells, cell lines, and cell preparations of the invention, and optionally one or more pharmaceutically acceptable carriers, excipients, or diluents. The pharmaceutical compositions may include a targeting agent to target cells to particular tissues or organs.

Cells, cell lines, and cell preparations may be used to screen for potential therapeutics that modulate development or activity of such cells or cells differentiated therefrom. In yet another aspect, there is provided herein a method for screening compounds including small molecules that affect the function of the cells. The method can include incubating components comprising a test compound and at least one cell under conditions sufficient to allow the components to interact; and determining the effect of the compound on a function of a cell before and after incubating with the test compound. A function of a cell may be modulated (e.g., inhibited or stimulated) by the test compound. By way of a non-limiting example, cell differentiation, gene expression, production of growth factors, response to growth factors, and cell membrane permeability may be modulated.

There is also provided herein a method for conducting a regenerative medicine business. Still further there is provided herein a method for conducting a cell business involving identifying agents that affect the proliferation, differentiation, function, or survival of canine lymphomic cells. An identified agent(s) can be formulated as a pharmaceutical preparation, and manufactured, marketed, and distributed for sale.

Thus, in still another aspect, there is provided herein methods for influencing the proliferation, differentiation, or survival of cells of the invention by contacting the cells with a test agent.

Also provided herein is a method of treating a subject comprising administering an effective amount of an agent to a subject with a disorder affecting or involving the proliferation, differentiation, function, or survival of the cells described herein. Also contemplated is a method for conducting a drug discovery business comprising identifying factors or agents that influence the proliferation, differentiation, function, or survival of cells of the invention, and licensing the rights for further development. Further, a method of providing drug development can include using cells or mitotic or differentiated progeny thereof as a source of biological components of cells in which one or more of these biological components are the targets of the drugs that are being developed.

In still another aspect, there is provided herein a bioassay, and/or kits including cells, or a mitotic or differentiated cells that are progeny of the cells. Also provided is a kit for transplantation of cells comprising a flask with medium and cells of the invention.

The cells, cell lines, and cell preparations are useful in rational drug design. In addition, kit for rational drug design can include cells obtained by a method described herein. In one embodiment, the kit comprises cells and instructions for their use in toxicity assays. The kit can be used for producing cells of the invention, or for producing an expanded cell preparation.

For convenience, certain terms employed in the specification and claims are collected here.

"Subject" or "patient" refers to an animal, preferably a mammal, to whom treatment, including prophylactic treatment, with the cells, cell preparations, and compositions of the present invention, is provided. For treatment of those conditions or disease states that are specific for a specific animal, the terms refer to that specific animal. In particular, the terms refer to a canine. The terms also include humans, domestic animals including dogs, horses, cows, sheep, poultry, fish, pigs, cats, and zoo animals.

"Cell line" refers to cultured cells that can be passaged at least one time without terminating. The invention contemplates cell lines that can be passaged at least 1, 2, 5, 10, 15, 20, 30, 40, 50, 60, 80, 100, and 200 times.

"Effective amount" refers to concentrations of components such as cells, preparations, or compositions effective for producing an intended result including treating a disease or condition with cells, preparations, and compositions of the invention, or for effecting a transplantation of cells within a subject to be treated.

The terms "administering" or "administration" refers to the process by which cells, preparations, or compositions of the invention are delivered to a subject for treatment purposes. Cells, preparations, or compositions may be administered a number of ways including parenteral (e.g. intravenous and intra-arterial as well as other appropriate parenteral routes), oral, subcutaneous, inhalation, or transdermal. Cells, preparations, and compositions of the invention are administered in accordance with good medical practices taking into account the subject's clinical condition, the site and method of administration, dosage, subject age, sex, body weight, and other factors known to physicians.

"Transplanting", "transplantation", "grafting" and "graft" are used to describe the process by which cells, preparations, and compositions of the invention are delivered to the site within the subject where the cells are intended to exhibit a favorable effect, such as repairing damage to a subject's tissues, treating a disease, injury or trauma, or genetic damage or environmental insult to an organ or tissue caused by, for example an accident or other activity. Cells, preparations, and compositions may also be delivered in a remote area of the body by any mode of administration relying on cellular migration to the appropriate area in the body to effect transplantation.

"Enriched" refers to a population of cells or a method which is at least 20+%, 30+%, 40+%, 50+%, 60+%, 70+%, 80+%, 85+%, 90+%, or 95+% effective, more preferably at least 98+% effective, most preferably 99+% effective. Therefore, a method that enriches for a given cell population, enriches at least about 20+%, 30+%, 40+%, 50+%, 60+%, 70+%, 80%, 85%, 90%, or 95% of the targeted cell population, most preferably at least about 98% of the cell population, most preferably about 99% of the cell population.

"Isolated" or "purified" refers to altered "by the hand of man" from the natural state i.e. anything that occurs in nature is defined as isolated when it has been removed from its original environment, or both. In one aspect, a population or composition of cells is substantially free of cells and materials with which it may be associated in nature. By substantially free or substantially purified is meant at least 50% of the population are the target cells, preferably at least 70%, more preferably-at least 80%, and even more preferably at least 90% are free of other cells. Purity of a population or composition of cells can be assessed by appropriate methods that are well known in the art.

"Gene therapy" refers to the transfer of new genetic information into cells for the therapeutic treatment of diseases or disorders. A foreign gene is transferred into a cell that proliferates to introduce the transferred gene throughout the cell population. Therefore, cells and compositions of the invention may be the target of gene transfer, since they may produce various lineages that will potentially express the foreign gene.

Development of OSW Canine Lymphoma Cell Line

To further accelerate the use of spontaneous cancers in dogs as a model system for new anticancer drug development and cancer cell biology, disclosed herein is a novel T-cell lymphoma cell line [deposited with the ATTC under Accession No. PTA-9116 on Mar. 20, 2008] and generally referred to herein as the "OSW cell line."

The cell line OSW was established from the malignant pleural effusion of a dog with peripheral T-cell lymphoma. The comparative molecular and biological properties of OSW (grown as a cell and xenograft) are described herein. The OSW cell line grows rapidly in vitro and is tumorigenic as a xenograft in SCID/NOD mice. The cell line has an oligoclonal TCRγ gene rearrangement, but does not express T-cell differentiation antigens. The OSW cell line contains several of the more common chromosomal aberrations reported previously in canine lymphoma [5,10,11], resulting in decreased copy number of p16/INK4a (also known as CDKN2A), RB1, and PTEN and increased copy number of MYC. As canine lymphoma has many similarities, both clinically and molecularly, to NHL in people, this cell line and xenograft will be useful for translational studies of novel therapeutics using spontaneous lymphoma in the dog as a model for human disease.

The immunoprofile, as determined by flow cytometry, was as follows: positive for CD45, CD49d, CD18, CD11a; weakly positive for CD11b, CD11c, CD11d; and negative for CD45RA, CD1a, CD1c, CD3, TCRαβ, TCRγδ, CD4, CD5, CD8a, CD8b, CD90(Thy1), CD21, MHCII, CD14(TUK4), CD34, and MPO.

Immunocytochemistry of cytospin preparations was negative for cytoplasmic CD3, CD79a, and MPO, but was positive for CD20. The cell line had an oligoclonal T cell receptor gamma (TCRγ) gene rearrangement. Array comparative genomic hybridization (aCGH) and single locus probe (SLP) analysis showed that there were copy number increases of loci on dog chromosome 13 (CFA 13), and copy number decreases were evident for regions of CFA 11, 22, 26, 30 and 32, which include several of the more common chromosomal aberrations reported previously in canine lymphoma.

Materials and Methods

A 5.5-year-old male Airedale Terrier was referred to The Ohio State University Veterinary Teaching Hospital in February 2004 for evaluation of lethargy and mandibular lymphadenopathy. The dog initially presented to the referring veterinarian two months previously for respiratory distress that responded to prednisone. On presentation, the dog was thin with muscle wasting, dehydration, muffled heart and lung sounds, and generalized peripheral lymphadenopathy. The complete blood count showed a leukocytosis (23,700 WBC/μL), with a mature neutrophilia (18,700 neutrophils/μL) and a mild monocytosis (1,900 monocytes/4). The hemogram showed a hemoglobin concentration (9.9 g/dL), packed cell volume (28%), red blood cell (RBC) count (4.0×106/μL), and RBC indices (mean corpuscular volume, 69 fl; mean corpuscular hemoglobin concentration, 35.6 g/dL; red cell distribution width, 16.4%), indicative of a nonregenerative anemia. A serum biochemical profile revealed hypercalcemia (14.4 mg/dL), elevated alkaline phosphatase (220 IU/L), and hypoglycemia (72 mg/dL).

Thoracic radiographs showed severe pleural effusion with hilar lymphadenopathy. Thoracocentesis was performed and 1000 mL of serosanguinous fluid was removed. An abdominal ultrasound showed multicentric lymphadenopathy, small hypoechoic nodules throughout the spleen, and a diffusely hyperechoic and enlarged liver. A biopsy of an enlarged popliteal lymph node was performed. Histopathological examination showed that the normal architecture of the lymph node was obliterated by sheets of large round cells with a high nuclear to cytoplasmic ratio, mild anisocytosis and anisokaryosis and a mitotic index of two per hpf (400×). The majority of these cells stained positive for CD3 and CD18, and negative for CD79a, CD20, and BLA36. Scattered within these tumor cells were moderate numbers of lymphocytes that stained positive for CD79a and BLA36. Based upon World Health Organization classification criteria, the tumor was classified as a peripheral T-cell lymphoma, unspecified [4]. The dog was treated with the combination chemotherapy protocol, COAP (cyclophosphamide, vincristine, cytosine arabinoside, prednisone) [12]. The subject achieved a transitory partial response; however, the subject presented again three weeks later with dyspnea, progressive lymphadenopathy, a cranial mediastinal mass, and bilateral pleural effusion. Ultrasound-guided needle biopsy of the cranial mediastinal mass was done and thoracocentesis was performed, removing approximately 900 mL of serosanguinous fluid, an aliquot of which was used to establish the OSW cell line. Cytology of the cranial mediastinal mass and thoracic fluid was compatible with hematopoietic neoplasia. The dog had minimal response to further chemotherapy and was euthanized eight weeks after initial diagnosis due to progressive disease.

Establishment of the T-Cell Lymphoma Line "OSW Cell Line"

Cells from the pleural effusion were centrifuged, washed in RPMI 1640 medium, and cultured in T25 flasks in RPMI 1640 medium supplemented with 20% heat-inactivated fetal bovine serum (FBS), penicillin, streptomycin, and L-glutamine. The cultures were incubated at 37° C. in a humidified atmosphere of 5% $CO_2$. For the first three weeks, both adherent and non-adherent cells were passaged together weekly. After three weeks in culture, the non-adherent cell population was passaged and grown as a suspension culture consisting primarily of single cells and small clumps. The morphologic appearance of the cells was assessed on cytospin preparations stained with Wright's-Giemsa stain.

The OSW cell line was subsequently maintained in continuous culture for over one year. For storage, cells are kept at a concentration of $1$-$5 \times 10^6$ cells/ml in 90% RPMI 1640 (supplemented with 20% FBS) and 10% DMSO and stored in liquid nitrogen. Immunophenotyping of the OSW cell line was determined on exponentially growing cells by two different laboratories (MJB, WV). Experiments were performed at least twice by each laboratory. Flow cytometry was carried out using the antibodies listed in Table 1. The sources of these reagents and the methods used have been described in detail elsewhere [13].

TABLE 1

Cell surface makers analysis and immunocytochemical staining

| Antigen | Clone |
| --- | --- |
| IgG1 (controls) | W3/25 |
| CD1a | CA9.AG5 |
| CD1c | CA13.9H11 |
| CD3 | CA 17.2 A12 |
| CD3ε | CD3-12 |
| CD4 | YKIX 302.9 |
| CD4 | CA13.1E4 |
| CD5 | YKIX 322.3 |
| CD8 | YCATE 55.9 |
| CD8 | CA9.JD3 |
| CD8 | CA15.4G2 |
| CD11a | CA11.4D3 |
| CD11a | CA16.1B11 |
| CD11b | CA16.3E10 |
| CD11c | CA11.6A1 |
| CD11d | CA11.8H2 |
| CD14 | TUK 4 |
| CD18 | YFC 118.3 |
| CD18 | CA1.4E9 |
| CD20 | polyclonal |
| CD21 | B-ly4 |
| CD21 | CA2.1D6 |
| CD34 | 1 H6 |
| CD45 | YKIX 716.13 |
| CD45 | YKIX 716.13 |
| CD45 | CA12.10C12 |
| CD45RA | CA4.1D3 |
| CD49-like (VLA-4) | CA4.5B3 |
| CD54 (ICAM-1) | CL18.1D8 |
| CD79a (MB-1) | HM57 |
| CD90 (Thy-1) | CA1.4G8 |
| MHC II | YKIX 3342 |
| MHC II | CA2.1C12 |
| TCR αβ | CA15.8G7 |
| TCR γδ | CA20.8H1 |
| TCR γδ | CA20.6A3 |
| MPO | CA25.10A6 |

The expression of four intracytoplasmic antigens also was assessed on cytospin smears of OSW cells as described previously [13]. The antibodies used for immunocytochemistry were CD3-12 (Serotec, Oxford, UK), HM-57 (Dako, Carpenteria, Calif.), CD20, and anti-canine myeloperoxidase (MPO) antibody 10A6. CD3-12 and HM-57 recognize conserved cytoplasmic peptide sequences of the CD3ε and CD79a antigens, respectively. The CD20 antibody used is an epitope-specific rabbit antibody that recognizes a highly conserved cytoplasmic peptide sequence of CD20. The MPO antibody (10A6) is a canine specific anti-MPO mouse monoclonal antibody. MPO is present in an intracytoplasmic location.

Histopathology and Immunohistochemistry

Primary tumor biopsy (lymph node and mediastinal mass) and mouse xenograft tissues were processed for routine histology by fixation in 10% neutral-buffered formalin followed by paraffin embedding and sectioning. Sections were stained with hematoxylin and eosin for microscopic examination. For immunophenotyping, paraffin-embedded sections were processed according to standard protocols before immunostaining [14]. Primary antibodies, anti-CD3 (rabbit polyclonal, Dako, Carpinteria, Calif., USA), -CD79a (clone HM57, Dako), -CD20 (rabbit polyclonal, Lab Vision Corp., Fremont, Calif.), and -BLA36 (clone A27-42, Dako) were used. Tumors were classified using the revised World Health Organization classification [4] based on morphological and immunohistochemical staining criteria.

Polymerase Chain Reaction for Antigen Receptor Rearrangements (PARR)

The presence of a T-cell receptor gamma (TCRγ) rearrangement was detected by PARR (PCR for clonal antigen receptor rearrangements) as described in Burnett et al [15]. The only change from the described methods was the replacement of the TCRγ primers with the following sequences, which were derived by examining cDNA and the published canine genome:

DPA ctgttgktgcagaarctggagaag (forward primer) [SEQ ID No. 1];

DPB aaccctgagaattgtgccaggac (reverse primer) [SEQ ID No. 2];

DPC gagttactataatcctggtamcttctg (reverse primer) [SEQ ID No. 3].

All three primers were included in the same reaction. The sample was amplified by two sets of primers for immunoglobulin gene segments in two separate reactions, and three primers for TCRγ gene segments in a single reaction. DNA positive control reaction was also run to ensure adequate DNA in the sample. A reaction was considered positive (clonal) if one or more dominant and discrete PCR products were present on the gel after electrophoresis, and the intensity of the band(s) was similar to the positive control. A reaction was considered negative if no bands, a diffuse smear or a ladder of faint bands was observed.

Cytogenetic Analysis

Generation of Chromosome Preparations

Five million cells were aspirated from a turbid suspension culture of OSW cells, pelleted, resuspended in complete medium supplemented with 25 ng/ml of Karyomax (Invitrogen, Carlsbad, Calif., USA) and incubated for 18 h at 38° C. The cells were recovered by centrifugation and divided equally into two tubes, one was used to isolate genomic DNA for array comparative genomic hybridization (aCGH) and the second was harvested for chromosome preparations by routine procedures [16].

Array CGH and Single-Locus Probe (SLP) FISH Analysis

Array CGH analysis was performed as described previously [17,18] using a genome-wide microarray comprising BAC clones representing 310 unique loci distributed at ~10 Mb intervals throughout the dog genome, including 30 clones harboring canine orthologs of human cancer-related genes. An equimolar mix of constitutional DNA from 40 clinically normal female dogs of four diverse breeds was used as the reference probe. Tumor and reference DNA probes were labeled with Cyanine-3-dCTP or Cyanine-5-dCTP (Perkin Elmer, Wellesley, Mass.), using a BioPrime Array CGH Labeling System (Invitrogen) following the manufacturer's recommendations. Array hybridization and image acquisition was performed as described previously [17]. Fluorescence intensities were calculated for each spot after local background subtraction, block-normalized to a mean 1:1 ratio on the autosomal clones, and ratios of normalized values established. Loci with confidence levels <0.1 or replicates with standard deviation >0.3 were excluded. The mean fluorescence ratio of replicates representing each locus was then converted to a $\log_2$ ratio in order to weight genomic gains and losses equally, and plotted graphically. A dye-swap experiment was similarly performed, and the results from both experiments were combined. Regions of copy number gain and loss were then identified using the aCGH Smooth algorithm [19]. Ten BAC clones, representing loci with a range of apparently normal and abnormal copy number ratios in aCGH, were differentially-labeled and hybridized onto metaphase chromosome preparations and interphase nuclei from the OSW cell line, as described elsewhere [20]. The same panel of clones was similarly hybridized onto chromosome preparations from a clinical healthy donor, to confirm the normal (n=2) copy number of each locus. Probe enumeration was performed on 30 tumor cells for each probe. Results were scored by two independent investigators, and aCGH and FISH data were then compared to demonstrate cross validation.

Xenografted Tumor Cell Growth in NOD/SCID Mice and Bioluminescent Imaging

Animals and Lymphoma Cell Inoculations

Immunodeficient SCID-NOD (NOD CB17-PRKDC-SCID/J) mice (Jackson Laboratory, Bar Harbor, Me., USA) were housed in the animal facility of the College of Veterinary Medicine at The Ohio State University, Columbus, Ohio. Mice were housed in microisolator cages, and were provided food pellets and water ad libitum. Animal care procedures were approved by the Institutional Laboratory Animal Care and Use Committee using criteria based on both the Animal Welfare Act and the Public Health Service's 'Guide for the Care and Use of Laboratory Animals'. OSW cells were transduced with a lentiviral vector expressing dual reporter genes luciferase/yellow fluorescent protein (YFP/Luc), as described previously [21]. Following transduction, the cells were bulk sorted using a BD FACSAria (Becton Dickinson) cell sorter (Heart and Lung Research Institute, The Ohio State University). Male mice (5 weeks-of-age) were injected intraperitoneally with approximately $5 \times 10^6$ cells suspended in RPMI 1640 medium. Controls were inoculated with medium alone. Complete necropsies were performed on all mice.

In Vitro, In Vivo and Ex Vivo Imaging

For in vitro imaging, bioluminescent cells were serially diluted two-fold from 10,000 to approximately 5 cells per well and plated in triplicates in a clear 96-well plate (Costar, Corning, N.Y., USA). D-Luciferin (Xenogen, Alameda, Calif.) at 150 ug/ml in medium was added to each well and imaged after five minutes using the IVIS® Imaging System (Xenogen).

For in vivo imaging mice were injected with D-luciferin dissolved in DPBS intraperitoneally at 150 mg/kg. Isoflurane was used for induction and maintenance of anesthesia. Mice were placed in the light-impermeable imaging chamber of the IVIS imaging system and the photons emitted from luciferase-expressing cells were quantified and analyzed using Living Image software version 2.50 (Xenogen).

For ex vivo imaging, luciferin was injected into the mice immediately prior to necropsy, tissues were collected after humane euthanasia and imaged.

Cytotoxicity and Proliferation Assays $1-2 \times 10^4$ cells were seeded in 96-well plates in quadruplicates to a final volume of 200 μL/well. Cells were treated with doxorubicin hydrochloride (Ben Venue Laboratories-Novation, Bedford, Ohio, USA) or vincristine sulfate (Mayne Pharma Pty Ltd., Mulgrave VIC, Australia) at varying concentrations of drug or vehicle control for 72 h. Cell proliferation and viability was determined using the WST-1 assay, which quantifies the reduction of the tetrazolium salt WST-1 by mitochondria in viable cells. Cell number was determined from absorbance values of known numbers of cells. At various time intervals, 20 μl of WST-1 reagent (Roche, Indianapolis, Ind., USA) was added to each well and incubated for 2 to 4 h at 37° C. The absorbance of the reaction product, after background subtraction, was measured at 450 nm on a Spectra Max M2 plate reader (Molecular Devices, Sunnyvale, Calif., USA). Each experiment was repeated at least three times.

Generation of Growth Curve

Cells were plated to achieve a plating density of $5 \times 10^4$ cells suspended in 300 μl of culture medium per well of a 48-well plate. Cells were incubated at 37° C. in a humidified atmosphere of 95% air and 5% $CO_2$. Cells in triplicate wells were counted every 24 h. The values obtained were plotted on a log-linear scale. The population-doubling time was determined from the exponential phase of the growth curve.

Results—Morphology of Primary Lymphoma (Peripheral Lymph Node, Mediastinal Mass, and Malignant Effusion)

The histopathological diagnosis of a peripheral lymph node biopsy from the dog was peripheral T-cell lymphoma. Immunohistochemical staining of the lymph node biopsy showed that the majority of neoplastic cells stained positive for CD3 and CD18 and were negative for CD20, CD79a, and BLA36, consistent with a T cell origin. Twenty to 30% of the round cells stained positive for CD79a. These cells were morphologically distinct from the neoplastic cells and were interpreted as normal infiltrating lymphocytes.

The morphology (FIG. 1A) and immunohistochemical staining pattern of the mediastinal mass was similar to the lymph node; however, there were fewer infiltrating lymphocytes.

The effusion cells consisted mostly of large, individual, exfoliated round cells with a high nuclear to cytoplasmic ratio (FIG. 1B).

Nuclei were eccentric, round to oval, and had fine chromatin and 1-3 large prominent nucleoli that varied in size and shape. The cytoplasm was abundant and was medium blue with occasional small clear vacuoles. Some cells contained round to rod shaped eosinophilic inclusions. Moderate numbers of mitotic figures were present.

Establishment of the OSW Cell Line

Tumor cells grew readily even without the addition of growth factors. Initially, two populations of cells were identified, an adherent spindle cell population, resembling fibroblasts, and a non-adherent round cell population. The two cell populations were grown together the first three weeks, then the cells growing in suspension were passaged alone. The round cell population continued to grow as a suspension culture and was passaged weekly thereafter and cell aliquots cryopreserved periodically. The cells have now been in culture for several years. The OSW cell line has a doubling time of approximately 24 h during exponential growth under standard culture conditions. The cell line shows a growth pattern of single large, round non-adherent cells that sometimes grow in small clusters.

Morphology and Immunophenotype of the OSW Cell Line

OSW cells were large round cells in culture, displaying moderate anisocytosis and anisokaryosis (FIG. 1C).

Nuclei were large, round, oval, or cleaved, with fine reticular chromatin and prominent, single to multiple variably sized and shaped, nucleoli. The cytoplasm was moderately basophilic. Cytoplasmic blebbing and punctuate vacuoles was more common than in the primary effusion cells, while mitotic figures and binucleate cells were less common. The OSW cell line had only generalized leukocyte markers on flow cytometric assessment.

The immunophenotype was: CD45+, CD45RA−, CD49d+, CD18+, CD11a+, CD11b 42% subpopulation with weak, continuous expression, CD11c 17% subpopulation with weak, continuous expression, CD11d 40% subpopulation with weak, continuous expression, CD1a−, CD1c−, CD3−, TCRαβ−, TCRγδ−, CD4−, CD5−, CD8a−, CD8b−, CD90(Thy 1)−, CD21−, MHCII−, CD14(TUK4)−, CD34 (1H6)−, and MPO (10A6)−. Similar flow cytometric immunophenotyping results were obtained in two different experiments repeated in two different laboratories. Immunocytochemistry of cytospins of the cell line indicated that the cells were negative for cytoplasmic CD3, CD79a, and MPO, but were positive for CD20.

Polymerase Chain Reaction for Antigen Receptor Rearrangements (PARR)

PCR analysis for immunoglobulin heavy chain (IgH) and T cell receptor gamma (TCRγ) gene rearrangements yielded an oligoclonal result (three bands) for the TCRγ gene and a negative result for the IgH gene (FIG. 2).

Identical results were obtained using cDNA derived from the lymph node biopsy sample and from both early and late passage OSW cells.

Array CGH and Single-Locus Probe Fish Analysis

Chromosome counts of 30 metaphase spreads from the OSW cell line indicated a range of 73-78 chromosomes (Canis familiaris, 2n=78) with a modal chromosome number of 75 (83% of cells). No remarkable findings were evident from conventional cytogenetics analysis, other than the recurrent presence of a third copy of almost the full length of CFA 13.

Data resulting from aCGH analysis of the OSW cell line are shown in FIG. 3, indicating an increase in copy number of the majority of clones representing CFA 13, and copy number decreases for regions of CFA 11, 22, 26, 30 and 32.

Single locus probe (SLP) analysis of a panel of ten BAC clones, performed in two five color FISH reactions (FIGS. 4A and 4B) correlated with the copy changes revealed by aCGH. Copy number profiles were highly consistent between individual cells analyzed at random from the tumor cell population. Over 95% of OSW cells analyzed showed no detectable signal for the CFA 11 marker, indicating homozygous deletion of the p16/INK4a gene (as compared to n=2 in the control). More than 90% of cells assessed showed the expected normal copy number of n=2 for clones representing regions of CFA 1, 5, 6, 15, 16 and 18, and an increased copy number of n=3 for the CFA 13 (MYC gene) marker; however SLP analysis also revealed that the additional copy of CFA 13 was not a full-length copy (consistent with aCGH data). Copy number decreases of loci representing CFA 22 (RB1 gene) and CFA 26 (PTEN gene) were detected in approximately 95% and 88% of OSW cells respectively.

Although the probe representing CFA 15 showed a normal copy number status (n=2), SLP analysis revealed that the second copy of CFA 15 had undergone a major structural alteration, resulting in the generation of a chromosome structure markedly longer than the normal CFA 15 homologue. The derivative chromosome also showed a consistently stronger FISH signal for the CFA 15 marker. While not wishing to be bound by theory, the inventor herein believes that this is likely to be the result of an abnormal chromosome fusion event coupled with an intrachromosomal amplification, and further analysis can determine the exact nature of this structure. The SLP data are summarized in FIG. 4C.

In Vitro Chemosensitivity

The in vitro chemosensitivity of the OSW cell line to doxorubicin and vincristine was determined. A dose-dependent inhibition of cell growth was demonstrated by both cytotoxic drugs. Doxorubicin had an inhibitory concentration 50% (IC50) of 0.5 µM and vincristine an IC50 of 0.4 µM (data not shown).

Tumorgenicity and Growth in NOD/SCID Mice and Bioluminescent Imaging

Serially diluted OSW cells transduced with lentiviral vectors expressing a dual reporter luciferase/yellow fluorescent protein gene were visualized using bioluminescent imaging. The minimum number of detectable cells was between 312 and 625 cells per well (FIG. 5A).

Bioluminescent OSW cells injected intraperitoneally and monitored using bioluminescent imaging successfully engrafted and produced tumors in 100% (6/6) of the mice. Tumor cells engrafted within a week after injection and bioluminescent imaging revealed progressive tumor growth for up to four weeks as shown by a representative mouse (FIG. 5B).

In vivo imaging at week 4 showed a diffuse growth of lymphoma in the abdominal cavity. Ex vivo imaging confirmed the presence of tumor in the mesentery, liver, lungs, peri-renal fat, and subcutaneously at the site of injection (FIG. 5C).

Diffuse mesenteric tumors were noted in all the mice on gross examination. Subcutaneous tumors at the site of injection were present in 3/6 mice. Histopathologic evaluation of the tissues revealed the presence of tumor cells in the mesentery (6/6), pancreas (6/6), liver (4/6), spleen (4/6) lungs (3/6), peri-renal fat (6/6), and invading the small intestine (1/6). In the mesentery and pancreas, solid sheets of neoplastic round cells replaced most of the normal cells. In the liver and lungs there were scattered microscopic foci of neoplastic cells. The tumors contained cells with a high nuclear to cytoplasmic ratio, moderate anisocytosis and anisokaryosis, and a mitotic index of 4 per hpf (FIG. 1D).

There was marked multifocal necrosis within the tumors. The majority of large neoplastic cells stained negative for CD3, CD20, and CD79a and positive for CD18. Overall, the histopathologic findings were consistent with an intermediate grade lymphoma.

Discussion

In one aspect, there is provided herein a novel canine lymphoma cell line derived from the malignant pleural effusion of a dog with peripheral T-cell lymphoma. The dog initially presented with peripheral lymphadenopathy and pleural effusion and had a partial response to combination chemotherapy; however, the disease progressed rapidly, typical of most intermediate- and high-grade T-cell lymphomas seen commonly in the dog. The morphology of OSW cells was similar to that of the primary pleural effusion cells. Study of rearrangement of the IgH and TCRγ genes showed the identical oligoclonal TCRγ rearrangement in early and late passage OSW cells and the primary lymph node tumor cells.

The OSW cells do not express T- or B-cell receptor antigens as assessed by flow cytometry; however, CD20 expression could be detected using immunocytochemistry. In contrast, the primary tumor expressed CD3 and was negative for the B-cell antigens CD79a, BLA36, and CD20 by immunohistochemistry.

Loss of expression of normal T-cell antigens is common in human T-cell leukemias [22] and has been reported in canine T-cell leukemias [23]. Co-expression of B- and T-cell lineage markers has been reported in both human and canine lymphomas [15, 24-27]. Based on the clinical presentation of the subject (including hypercalcemia and presence of a cranial mediastinal mass), initial immunophenotype of the primary tumor, and an identical oligoclonal TCRγ gene rearrangement that was present in the primary tumor and early and late passage OSW cells, the inventor has now discovered that the OSW cell line is of T-cell origin and represents a canine T-cell lymphoma cell line.

Array CGH of the OSW cell line demonstrated a range of recurrent numerical cytogenetic aberrations, including copy number increases spanning the majority of CFA 13, and smaller regions of copy number decrease on CFA 11, 22, 26, 30 and 32. The OSW cell line contains several of the recurrent chromosomal aberrations previously reported in canine lymphoma, most notably copy number gain of CFA 13 and loss of CFA 11 [5,10,11]. SLP analysis indicated that the copy changes revealed by aCGH also were evident in the tumor cell population. CFA 13 is evolutionarily related to sites on two human chromosomes, HSA 8q23-qtel and HSA 4 pproxqprox [28-30], and harbors both the MYC and KIT protooncogenes [31]. Activation of human c-myc has been shown to be a common event in intermediate- and high-grade NHL [32] and dysregulation of c-kit occurs in some human lymphoma/leukemias and other cancers [33-37].

CGH analysis of the OSW cell line revealed copy number losses on CFA 11, including the site of the canine p16/INK4a gene. SLP analysis confirmed copy number decrease of the BAC clone representing this gene in >95% of OSW cells analyzed. CFA 11 shares extensive regions of conserved synteny with HSA 9, which harbors the human p16/INK4a locus. In humans, alterations leading to p16 inactivation (deletion or promoter methylation) are relatively common in adult and pediatric sporadic acute T-cell leukemias and in endemic adult T-cell lymphoma secondary to HTLV-I infection [38-42]. Deletion or promoter methylation leading to p16 inactivation also is observed in some types of B-cell NHL; most commonly in blastoid mantle cell lymphoma [43,44], less frequently in progression of mucosal associated lymphoid tissue (MALT) lymphoma or follicular lymphoma to DLBCL [42], and only sporadically in high-grade tumors [42,45,46].

Recently Fosmire S P, Thomas R, et al, (submitted) 48 nodal canine B- and T-cell lymphomas were analyzed for p16/INK4a inactivation. Metaphase-based or array-based comparative genomic hybridization (CGH) analysis and Southern blotting were used, respectively, to identify gross genomic imbalances and to assess deletion of individual genes. Deletion of p16/INK4a (or loss of CFA11) was restricted to high-grade T-cell NHL (lymphoblastic T-cell lymphoma and peripheral T-cell lymphoma—not otherwise classified).

Thus, the OSW cell line contains two of the most common and best described recurrent chromosomal aberrations identified in spontaneous canine lymphoma. Furthermore, these chromosomal aberrations were within minimal regions of loss that are syntenic between the canine and human CMYC and INK4 loci, containing the c-myc and p16/INK4a genes, respectively, two genes strongly associated with human lymphoma pathogenesis.

Figure 4B:
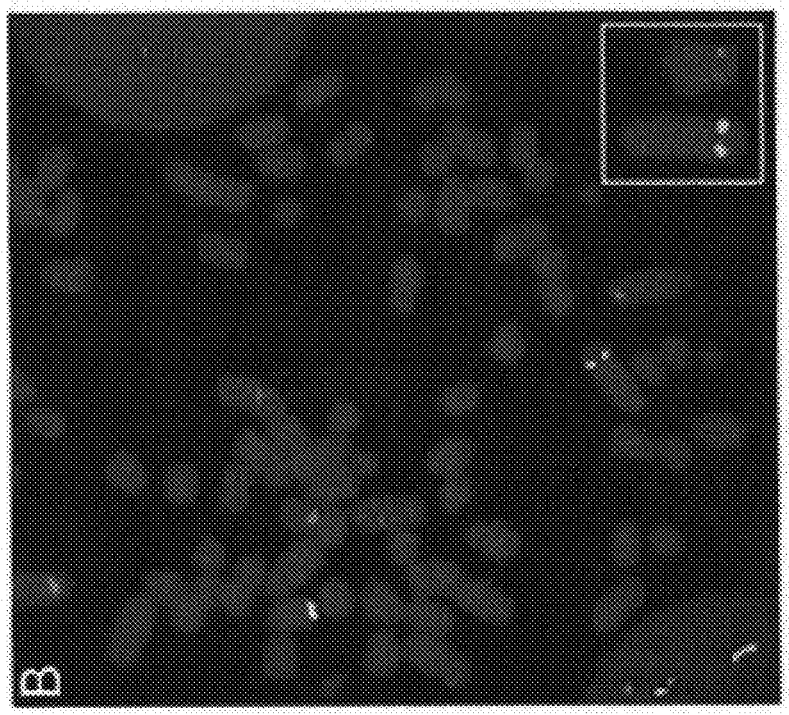
FIG. 4B—SLP image of BAC clones selected from CFA 1 (BCL2—aqua), CFA 5 (TP53—red), CFA 15 (CDK4—pink), CFA 22 (RB1—orange) and CFA 26 (PTEN—green), demonstrating copy number decrease of the clones representing RB1 (CFA 22) and PTEN (CFA 26). Despite a normal copy number for the CFA 15 clone, SLP data revealed the existence of one apparently normal copy of CFA 15 (inset, right chromosome) and second copy (inset, left chromosome) which has a much stronger FISH signal and has also undergone a structural change associated with a marked increase in length.
Figure 4A:
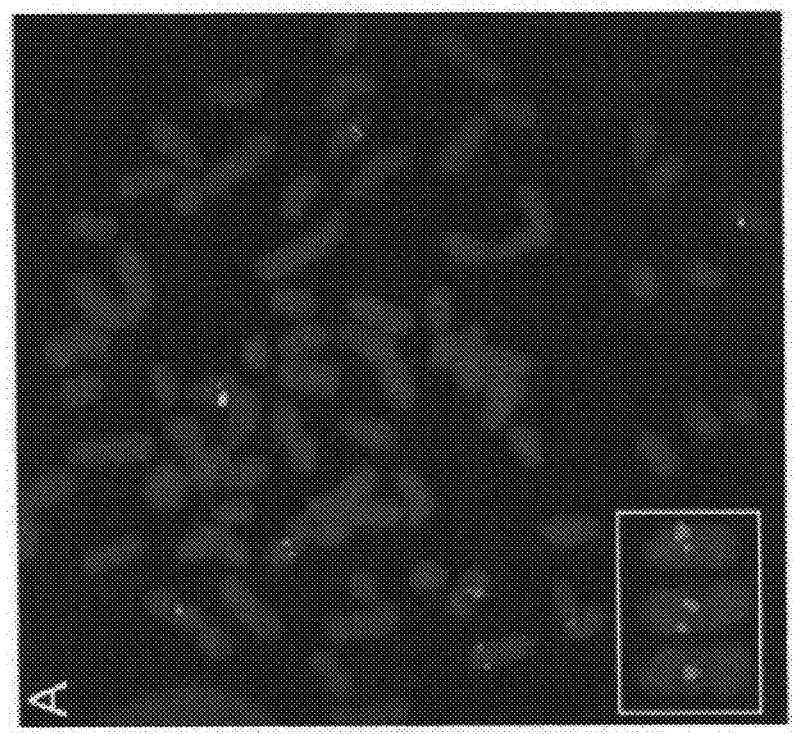
FIG. 4A—SLP image of BAC clones representing regions of CFA 6 (TSC2—red), CFA 11 (p16/INK4a—orange), CFA 13 (MYC—green), CFA 16 (aqua) and CFA 18 (HRAS—pink) hybridized onto a metaphase preparation from the OSW line. These data indicate abnormal copy number of the clones representing CFA 13 (MYC, n=3) and CFA 11 (p16/INK4a, n=0), as was detected by aCGH. The three copies of CFA 13 have been enlarged and placed in the insert, demonstrating that one copy (here shown on the far right) in each cell analyzed appeared to be truncated due to an internal deletion. The absence of any signal for the p16/INK4a (CFA 11) clone was evident in >95% of OSW cells analyzed.
Figure 4C:
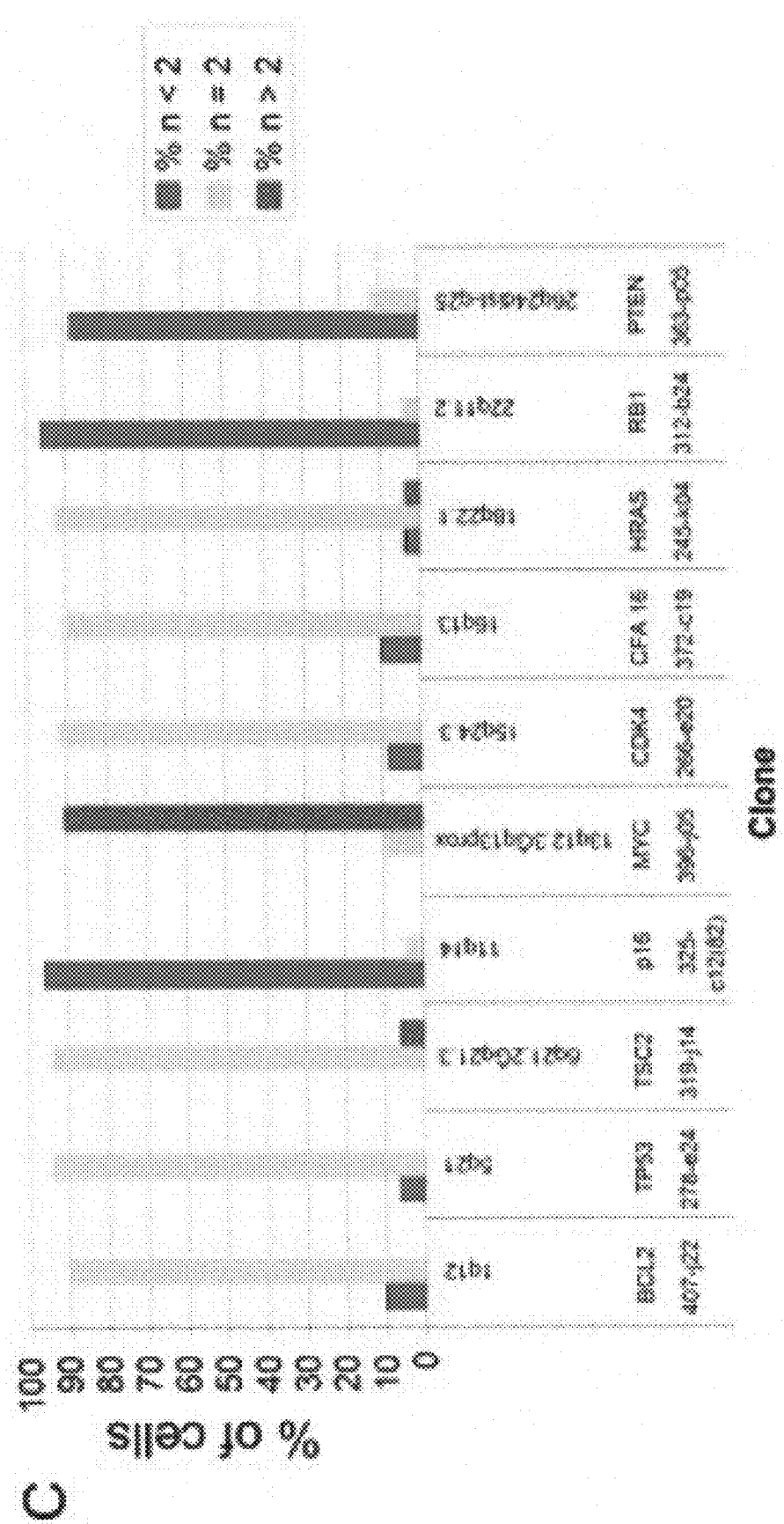
FIG. 4C—Summary of copy number distribution for a panel of 10 SLPs selected from the BAC array and hybridized onto cells from the OSW line. Data were compiled from a minimum of 30 cells for each SLP.

Additionally, SLP analysis demonstrated copy number decreases of clones containing the cancer associated genes RB 1 (on CFA 22) and PTEN (on CFA 26) (FIG. 4B).

The extent of these losses was suggestive of heterozygous deletion of both these key loci. Rb inactivation, whether caused by p16 inactivation or by other mechanisms, is a strong indicator of prognosis and predictor of therapeutic response for canine NHL[11]. Loss of heterozygosity of the PTEN gene occurs in a subset of human NHLs [47].

Bioluminescent imaging is particularly advantageous for monitoring in vivo growth of hematopoietic cell lines that disseminate widely in their hosts as xenografts. The inventor herein was able to detect less then 1000 YFP/Luc transduced OSW cells in vitro using bioluminescent imaging. OSW cells were highly tumorigenic in SCID/NOD mice, being well established in their hosts within one week, as determined by bioluminescent imaging. The use of in vivo bioluminescent imaging allowed for the serially monitoring of tumor growth in the same mice over time.

Taken together, these experiments demonstrate the value of the cell line in investigating lymphomas and identifying test agents for therapeutic activity. As such, the present invention also relates to one or more of the following:

A preparation of canine lymphomic cells characterized at least by being immunoreactive with markers for lymphomic cells.

Canine lymphomic cells induced to differentiate into cells of a variety of lineages in vitro or in vivo. Cells differentiated in vitro from a canine lymphomic cell. Lymphomic cells or cells differentiated or derived therefrom, cultured either transiently or maintained as a cell line. Cells, cell lines, and cell preparations derived from or comprised of cells that have been genetically modified either in nature or by genetic engineering techniques in vivo or in vitro from at least the cell lines described herein. A cell line for study of canine spontaneous lymphoma.

An in vitro model for comparative and translational lymphoma research comprising at least the cell lines described herein. A preclinical model for the development of canine therapies comprising at least the cell lines described herein.

A method for developing particular animal models of disease comprising using at least the cell lines described herein. A method for isolating lymphoma cells from canines and for establishing canine lymphoma cell lines comprising determining one or more developmental stages that enable maintenance and expansion of canine lymphoma cells.

A method for obtaining a purified canine lymphomic cell line, comprising culturing cells from a canine lymphomic cell under conditions to promote proliferation of such cells. A method additionally including inducing differentiation of the cells. A method including making cell preparations or lines derived at all stages of development under the same culture conditions.

A method for producing a genetically transformed animal as a model for human disease at least comprising using the cell lines described herein.

Pharmaceutical products produced by the cells, cell lines, or cell preparations, or mitotic or differentiated cells that are progeny of the cells described herein. Cells, cell lines, and cell preparations used in cell therapies and gene therapies aimed at alleviating disorders and diseases. A pharmaceutical composition comprising preparations derived from the cells and cell line and a pharmaceutically acceptable carrier, excipient, or diluent.

A method of treating a subject with a condition comprising transferring to a subject an effective amount of a therapeutic agent derived from at least the cells described herein. The cells, cell lines, and cell preparations used as immunogens that are administered to a heterologous recipient. The cells, cell lines, and cell preparations used to prepare model systems of disease, in particular canine and human diseases. The cells, cell lines, and cell preparations used to produce growth factors, hormones, and the like.

Cells, cell lines, and cell preparations used to screen for potential therapeutics that modulate development or activity of such cells or cells differentiated therefrom.

A method for screening compounds including small molecules that affect the function of cells, including incubating components comprising a test compound and at least one cell as described herein under conditions sufficient to allow the components to interact; and determining the effect of the compound on a function of a cell before and after incubating with the test compound. A method where a function of at least one cell is modulated by the test compound. A method where the modulation comprises inhibition or stimulation. A method where the modulation comprises at least one or more of cell differentiation, gene expression, production of growth factors, response to growth factors, and cell membrane permeability. A method for conducting a regenerative medicine business by identifying agents that affect the proliferation, differentiation, function, or survival of canine lymphomic cells described herein. A method where an identified agent is formulated as a pharmaceutical preparation.

A method for influencing the proliferation, differentiation, or survival of cells by contacting the cells with a test agent. A method of treating a subject comprising administering an effective amount of an agent identified in accordance with a method of the invention to a subject with a disorder affecting or involving the proliferation, differentiation, function, or survival of cells. A method for conducting a drug discovery business comprising identifying factors or agents that influence the proliferation, differentiation, function, or survival of cells. A method of providing drug development wherein cells described herein or mitotic or differentiated progeny thereof, are used as a source of biological components of cells in which one or more of these biological components are the targets of the drugs that are being developed.

A method of providing a bioassay comprising using at least the cells described herein. A kit including cells a mitotic or differentiated cells that are progeny of the cells. An antibody that specifically bind to a polypeptide isolated from the cell line.

A method of detecting a canine peripheral T-cell lymphoma comprising: a) contacting one or more antibodies that specifically bind to a polypeptide isolated from the cell line with a test sample under conditions that allow peripheral T-cell lymphocyte/antibody complexes to form; and b) detecting peripheral T-lymphocyte/antibody complexes; wherein the detection of peripheral T-lymphocyte/antibody complexes is an indication that a canine peripheral T-lymphocyte is present in the sample and the absence of peripheral T-lymphocyte/antibody complexes is an indication that a canine peripheral T-lymphocyte is not present in the sample. A method where the one or more antibodies are monoclonal antibodies, polyclonal antibodies, or antibody fragments. A method where the sample is lymph node or tissue aspirate, serum, whole blood, cellular suspension, or fluid effusion.

A method of treating a peripheral T-cell lymphoma, comprising administering the antibody produced using at least one cell described herein to the subject.

While the invention has been described with reference to various and preferred embodiments, it should be understood by those skilled in the art that various changes may be made and equivalents may be substituted for elements thereof without departing from the essential scope of the invention. In addition, many modifications may be made to adapt a particular situation or material to the teachings of the invention without departing from the essential scope thereof. Therefore, it is intended that the invention not be limited to the particular embodiment disclosed herein contemplated for carrying out this invention, but that the invention will include all embodiments falling within the scope of the claims.

REFERENCES

The citation of any reference herein is not an admission that such reference is available as prior art to the instant invention. Any publications mentioned in this specification are herein incorporated by reference. Any discussion of documents, acts, materials, devices, articles or the like which has been included in the present specification is solely for the purpose of providing a context for the present invention. It is not to be taken as an admission that any or all of these matters form part of the prior art base or were common general knowledge in the field relevant to the present invention as it existed before the priority date of each claim of this application.

1. Khanna C, Lindblad-Toh K, Vail D, London C, Bergman P, Barber L, et al. The dog as a cancer model. Nat Biotechnol 2006; 24:1065-6.
2. Hansen K, Khanna C. Spontaneous and genetically engineered animal models; use in preclinical cancer drug development. Eur J Cancer 2004; 40:858-80.

3. Vail D M, MacEwen E G. Spontaneously occurring tumors of companion animals as models for human cancer. Cancer Invest 2000; 18:781-92.
4. Valli V E, Jacobs R M, Parodi A L, Vernau W, Moore P F. Classification of Hematopoietic Tumors of Domestic Animals, Second Series ed. Washington, D.C.: AFIP-American Registry of Pathology. 2002.
5. Thomas R, Smith K C, Ostrander E A, Galibert F, Breen M. Chromosome aberrations in canine multicentric lymphomas detected with comparative genomic hybridisation and a panel of single locus probes. Br J Cancer 2003; 89:1530-7.
6. Steplewski Z, Jeglum K A, Rosales C, Weintraub N. Canine lymphoma-associated antigens defined by murine monoclonal antibodies. Cancer Immunol Immunother 1987; 24:197-201.
7. Nakaichi M, Taura Y, Kanki M, Mamba K, Momoi Y, Tsujimoto H, et al. Establishment and characterization of a new canine B-cell leukemia cell line. J Vet Med Sci 1996; 58:469-71.
8. Momoi Y, Okai Y, Watari T, Goitsuka R, Tsujimoto H, Hasegawa A. Establishment and characterization of a canine T-lymphoblastoid cell line derived from malignant lymphoma. Vet Immunol Immunopathol 1997; 59:1120.
9. Ghernati I, Auger C, Chabanne L, Corbin A, Bonnefont C, Magnol J P, et al. Characterization of a canine long-term T cell line (DLC 01) established from a dog with Sezary syndrome and producing retroviral particles. Leukemia 1999; 13:1281-90.
10. Hahn K A, Richardson R C, Hahn E A, Chrisman C L. Diagnostic and prognostic importance of chromosomal aberrations identified in 61 dogs with lymphosarcoma. Vet Pathol 1994; 31:528-40.
11. Modiano J F, Breen M, Valli V E, Wojcieszyn J W, Cutter G R. Predictive value of p16 or Rb inactivation in a model of naturally occurring canine non-Hodgkin's lymphoma. Leukemia 2006.
12. Couto C G, Lymphoma in the cat and dog. in: R W Nelson, Couto, C. G., (Ed.), Small Animal Internal Medicine St. Louis, Mo.: Mosby; 2003. pp. 1122-32.
13. Vernau W, Moore P F. An immunophenotypic study of canine leukemias and preliminary assessment of clonality by polymerase chain reaction. Vet Immunol Immunopathol 1999; 69:145-64.
14. Choi C, Kusewitt D F. Comparison of tyrosinase-related protein-2, S-100, and Melan A immunoreactivity in canine amelanotic melanomas. Vet Pathol 2003; 40:713-8.
15. Burnett R C, Vernau W, Modiano J F, Olver C S, Moore P F, Avery A C. Diagnosis of canine lymphoid neoplasia using clonal rearrangements of antigen receptor genes. Vet Pathol 2003; 40:32-41.
16. Breen M, Bullerdiek J, Langford C F. The DAPI banded karyotype of the domestic dog (*Canis familiaris*) generated using chromosome-specific paint probes. Chromosome Res 1999; 7:401-6.
17. Thomas R, Scott A, Langford C F, Fosmire S P, Jubala C M, Lorentzen T D, et al. Construction of a 2-Mb resolution BAC microarray for CGH analysis of canine tumors. Genome Res 2005; 15:1831-7.
18. Thomas R, Fiegler H, Ostrander E A, Galibert F, Carter N P, Breen M. A canine cancer-gene microarray for CGH analysis of tumors. Cytogenet Genome Res 2003; 102:254-60.
19. Jong K, Marchiori E, Meijer G, Vaart A V, Ylstra B. Breakpoint identification and smoothing of array comparative genomic hybridization data. Bioinformatics 2004; 20:3636-7.
20. Breen M, Hitte C, Lorentzen T D, Thomas R, Cadieu E, Sabacan L, et al. An integrated 4249 marker FISH/RH map of the canine genome. BMC Genomics 2004; 5:65.
21. Tannehill-Gregg S H, Levine A L, Nadella M V, Iguchi H, Rosol T J. The effect of zoledronic acid and osteoprotegerin on growth of human lung cancer in the tibias of nude mice. Clin Exp Metastasis 2006.
22. Jennings C D, Foon K A. Recent advances in flow cytometry: application to the diagnosis of hematologic malignancy. Blood 1997; 90:2863-92.
23. Avery P R, Avery A C. Molecular methods to distinguish reactive and neoplastic lymphocyte expansions and their importance in transitional neoplastic states. Vet Clin Pathol 2004; 33:196-207.
24. Pilozzi E, Pulford K, Jones M, Muller-Hermelink H K, Falini B, Ralfkiaer E, et al. Co-expression of CD79a (JCB117) and CD3 by lymphoblastic lymphoma. J Pathol 1998; 186:140-3.
25. Thomas R, Smith K C, Gould R, Gower S M, Binns M M, Breen M. Molecular cytogenetic analysis of a novel high-grade canine T-lymphoblastic lymphoma demonstrating co-expression of CD3 and CD79a cell markers. Chromosome Res 2001; 9:649-57.
26. Yao X, Teruya-Feldstein J, Raffeld M, Sorbara L, Jaffe E S. Peripheral T-cell lymphoma with aberrant expression of CD79a and CD20: a diagnostic pitfall. Mod Pathol 2001; 14:105-10.
27. Lai R, Juco J, Lee S F, Nahirniak S, Etches W S. Flow cytometric detection of CD79a expression in T-cell acute lymphoblastic leukemias. Am J Clin Pathol 2000; 113:823-30.
28. Breen M, Thomas R, Binns M M; Carter N P, Langford C F. Reciprocal chromosome painting reveals detailed regions of conserved synteny between the karyotypes of the domestic dog (*Canis familiaris*) and human. Genomics 1999; 61:145-55.
29. Yang F, O'Brien P C, Milne B S, Graphodatsky A S, Solanky N, Trifonov V, et al. A complete comparative chromosome map for the dog, red fox, and human and its integration with canine genetic maps. Genomics 1999; 62:189-202.
30. Breen M, Jouquand S, Renier C, Mellersh C S, Hitte C, Holmes N G, et al. Chromosome-specific single-locus FISH probes allow anchorage of an 1800 marker integrated radiation-hybrid/linkage map of the domestic dog genome to all chromosomes. Genome Res 2001; 11:1784-95.
31. Thomas R, Bridge W, Benke K, Breen M. Isolation and chromosomal assignment of canine genomic BAC clones representing 25 cancer-related genes. Cytogenet Genome Res 2003; 102:249-53.
32. Gaidano G, Dalla-Favera R. Biologic and molecular characterization of non-Hodgkin's lymphoma. Curr Opin Oncol 1993; 5:776-84.
33. Vakiani E, Cattoretti G, Colovai A I, Murty V V, Alobeid B, Bhagat G. CD117 expression in diffuse large B-cell lymphomas: fact or fiction? Pathol Int 2005; 55:716-23.
34. Sattler M, Salgia R. Targeting c-Kit mutations: basic science to novel therapies. Leuk Res 2004; 28 Suppl 1:S11-20.
35. Pruneri G, Ponzoni M, Ferreri A J, Freschi M, Tresoldi M, Baldini L, et al. The prevalence and clinical implications of c-kit expression in plasma cell myeloma. Histopathology 2006; 48:529-35.
36. Fletcher J A. Role of KIT and platelet-derived growth factor receptors as oncoproteins. Semin Oncol 2004; 31:4-11.

37. Advani A S. C-kit as a target in the treatment of acute myelogenous leukemia. Curr Hematol Rep 2005; 4:51-8.
38. Drexler H G. Review of alterations of the cyclin-dependent kinase inhibitor INK4 family genes p15, p16, p18 and p19 in human leukemia-lymphoma cells. Leukemia 1998; 12:845-59.
39. Delmer A, Tang R, Senamaud-Beaufort C, Paterlini P, Brechot C, Zittoun R. Alterations of cyclin-dependent kinase 4 inhibitor (p16INK4A/MTS1) gene structure and expression in acute lymphoblastic leukemias. Leukemia 1995; 9:1240-5.
40. Cayuela J M, Gardie B, Sigaux F. Disruption of the multiple tumor suppressor gene MTS1/p16(INK4a)/CDKN2 by illegitimate V(D)J recombinase activity in T-cell acute lymphoblastic leukemias. Blood 1997; 90:3720-6.
41. Yamada Y, Hatta Y, Murata K, Sugawara K, Ikeda S, Mine M, et al. Deletions of p15 and/or p16 genes as a poor-prognosis factor in adult T-cell leukemia. J Clin Oncol 1997; 15:1778-85.
42. Villuendas R, Sanchez-Beato M, Martinez J C, Saez A I, Martinez-Delgado B, Garcia J F, et al. Loss of p16/INK4A protein expression in non-Hodgkin's lymphomas is a frequent finding associated with tumor progression. Am J Pathol 1998; 153:887-97.
43. Swerdlow S H, Williams M E. From centrocytic to mantle cell lymphoma: a clinicopathologic and molecular review of 3 decades. Hum Pathol 2002; 33:720.
44. Pinyol M, Hernandez L, Cazorla M, Balbin M, Jares P, Fernandez P L, et al. Deletions and loss of expression of p16INK4a and p21 Wafl genes are associated with aggressive variants of mantle cell lymphomas. Blood 1997; 89:272-80.
45. Gronbaek K, de Nully Brown P, Moller M B, Nedergaard T, Ralfkiaer E, Moller P, et al. Concurrent disruption of p16INK4a and the ARF-p53 pathway predicts poor prognosis in aggressive non-Hodgkin's lymphoma. Leukemia 2000; 14:1727-35.
46. Geradts J, Andriko J W, Abbondanzo S L. Loss of tumor suppressor gene expression in high-grade but not low-grade non-Hodgkin's lymphomas. Am J Clin Pathol 1998; 109:669-74.
47. Herranz M, Urioste M, Santos J, Martinez-Delgado J B, Rivas C, Benitez J, et al. Allelic losses and genetic instabilities of PTEN and p73 in non-Hodgkin lymphomas. Leukemia 2000; 14:1325-7.
48. Drexler H G, Matsuo A Y, MacLeod R A. Continuous hematopoietic cell lines as model systems for leukemia-lymphoma research. Leuk Res 2000; 24:881-911.
49. Drexler H G, The Leukemia-Lymphoma Cell Line Facts Book, San Diego, Calif.: Academic Press; 2001
50. Moulton J E, Harvey, J. W., Tumors of lymphoid and hematopoietic tissue. in: J E Moulton, (Ed.), Tumors of Domestic Animals, Berkley: University of California Press; 1990. pp. 231-307.
51. Kaiser H E, Animal neoplasms: A systemic review. in: HE Kaiser, (Ed.), Neoplasms-comparative pathology in animals, plants and man, Baltimore: Williams and Wilkins; 1981. pp. 747-812.
52. Modiano J F, Breen M, Burnett R C, Parker H G, Inusah S, Thomas R, et al. Distinct B-cell and T-cell lymphoproliferative disease prevalence among dog breeds indicates heritable risk. Cancer Res 2005; 65:5654-61.
53. Vail D M, MacEwen, E. G., Young, K. M., Canine lymphoma and lymphoid leukemias. in: S J Withrow, MacEwen, E. G., (Ed.), Small Animal Clinical Oncology, Philadelphia: W.B. Saunders Co.; 2001. pp. 558-90.
54. Lindblad-Toh K, Wade C M, Mikkelsen T S, Karlsson E K, Jaffe D B, Kamal M, et al. Genome sequence, comparative analysis and haplotype structure of the domestic dog. Nature 2005; 438:803-19.

What is claimed is:

1. A method for identifying a compound or small molecule that modulates a function of peripheral T-cell lymphoma cells, comprising:
   measuring a function in at least one isolated canine peripheral T-cell lymphoma cell (OSW cell) having an ATCC Accession No. PTA-9116;
   incubating said at least one isolated OSW cell with a test compound or small molecule;
   measuring said function in said at least one OSW cell following incubation with said test compound or small molecule; and
   determining the difference in said function in said at least one OSW cell before and after said incubation with said test compound or small molecule;
   wherein a difference in function in said at least one OSW cell after said incubation as compared to before said incubation with said test compound or small molecule identifies said test compound or small molecule as a test compound or small molecule that modulates said function in peripheral T-cell lymphoma cells.

2. The method of claim 1, where said function being modulated is at least one of the functions selected from the group consisting of cell differentiation, gene expression, production of growth factors, response to growth factors, and cell membrane permeability.

3. A method of claim 1, wherein the test compound or small molecule is formulated as a pharmaceutical preparation.

4. A method of influencing the proliferation, differentiation, or survival of isolated canine peripheral T-cell lymphoma cells (OSW cells) having the ATCC Accession No. PTA-9116 comprising contacting said OSW cells with an agent demonstrated to influence proliferation, differentiation, or survival of peripheral T cell lymphoma cells.

5. A method of providing a bioassay comprising:
   measuring a biological function in an isolated canine peripheral T-cell lymphoma cell (OSW cell) having an ATCC Accession No. PTA-9116 under a first set of conditions;
   subjecting said biological function in said OSW cells to a second set of conditions;
   measuring said biological function in said OSW cell under the second set of conditions; and
   determining if said biological function differs between said first and second sets of conditions.

* * * * *

```
SEQUENCE LISTING

<160> NUMBER OF SEQ ID NOS: 3

<210> SEQ ID NO 1
<211> LENGTH: 24
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 1
ctgttgktgc agaarctgga gaag                                                24

<210> SEQ ID NO 2
<211> LENGTH: 23
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 2
aaccctgaga attgtgccag gac                                                 23

<210> SEQ ID NO 3
<211> LENGTH: 27
<212> TYPE: DNA
<213> ORGANISM: Artificial Sequence
```

-continued

```
<220> FEATURE:
<223> OTHER INFORMATION: Description of Artificial Sequence: Synthetic
      primer

<400> SEQUENCE: 3
gagttactat aatcctggta mcttctg                                              27
```